US012810988B2

(12) United States Patent
Song

(10) Patent No.: US 12,810,988 B2
(45) Date of Patent: Nov. 24, 2026

(54) SYSTEM INCLUDING SMART HOME MAT AND METHOD FOR CONTROLLING SAME

(71) Applicant: LG ELECTRONICS INC., Seoul (KR)

(72) Inventor: Wonkyu Song, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 18/844,486

(22) PCT Filed: Mar. 7, 2022

(86) PCT No.: PCT/KR2022/003171

§ 371 (c)(1),
(2) Date: Sep. 6, 2024

(87) PCT Pub. No.: WO2023/171827

PCT Pub. Date: Sep. 14, 2023

(65) Prior Publication Data

US 2025/0181139 A1 Jun. 5, 2025

(51) Int. Cl.
*G16H 20/30* (2018.01)
*G06F 3/01* (2006.01)
(Continued)

(52) U.S. Cl.
CPC ............. *G16H 20/30* (2018.01); *G06F 3/011* (2013.01); *G08B 25/016* (2013.01);
(Continued)

(58) Field of Classification Search
CPC ........ G06F 3/011; G06F 3/015; G06F 3/0304; G06F 3/041; G08B 25/016; G08B 25/002; H04N 21/42201; H04N 21/4223; H04N 21/44213; A63B 24/0062; A63B 24/0087; A63B 69/0035; A63B 71/0622; A63B 2024/0096; A63B 2071/0638;
(Continued)

(56) References Cited

U.S. PATENT DOCUMENTS

2017/0172331 A1* 6/2017 Publicover .............. B32B 7/022
2019/0118066 A1* 4/2019 Cardona ............ A63B 24/0062
(Continued)

FOREIGN PATENT DOCUMENTS

KR 10-1417622 B1 7/2014
KR 10-1592534 B1 2/2016
(Continued)

*Primary Examiner* — Adam R. Giesy
(74) *Attorney, Agent, or Firm* — Birch, Stewart, Kolasch & Birch, LLP

(57) ABSTRACT

A method for controlling a system including a smart home mat, according to an embodiment of the present invention, comprises the steps of: capturing an image of a user through a camera of a TV; generating a virtual avatar on the basis of the captured image; outputting a graphic image related to a virtual exercise environment, which induces the user located on the smart home mat to exercise, through a display of the TV; and controlling the graphic image related to the virtual exercise environment to be changed on the basis of at least one of exercise amount information about the user and health state information about the user.

10 Claims, 20 Drawing Sheets

(51) Int. Cl.

| | |
|---|---|
| ***G08B 25/01*** | (2006.01) |
| ***H04N 21/422*** | (2011.01) |
| ***H04N 21/4223*** | (2011.01) |
| ***H04N 21/442*** | (2011.01) |
| *A63B 24/00* | (2006.01) |
| *A63B 69/00* | (2006.01) |
| *A63B 71/06* | (2006.01) |

(52) U.S. Cl.

CPC ... *H04N 21/42201* (2013.01); *H04N 21/4223* (2013.01); *H04N 21/44213* (2013.01); *A63B 24/0062* (2013.01); *A63B 24/0087* (2013.01); *A63B 69/0035* (2013.01); *A63B 71/0622* (2013.01); *A63B 2071/0638* (2013.01); *A63B 2220/30* (2013.01); *A63B 2220/56* (2013.01); *A63B 2220/806* (2013.01); *A63B 2220/83* (2013.01); *A63B 2230/04* (2013.01); *A63B 2230/202* (2013.01)

(58) Field of Classification Search

CPC ............ A63B 2220/30; A63B 2220/56; A63B 2220/806; A63B 2220/83; A63B 2230/04; A63B 2230/202; A63B 21/4037; A63B 2024/009; A63B 2230/30; G16H 40/63; G16H 40/67; G16H 50/30; G16H 50/70; G16H 20/30; G06T 13/40; G06T 19/20

See application file for complete search history.

(56) References Cited

U.S. PATENT DOCUMENTS

| | | | | |
|---|---|---|---|---|
| 2019/0262664 | A1* | 8/2019 | Schindler ........... | A63B 24/0075 |
| 2025/0135287 | A1* | 5/2025 | Bergmann-Good ... | G16H 20/70 |

FOREIGN PATENT DOCUMENTS

| | | | |
|---|---|---|---|
| KR | 10-2017-0100335 | A | 9/2017 |
| KR | 10-2017-0109288 | A | 9/2017 |
| KR | 10-2019-0117099 | A | 10/2019 |
| KR | 10-2060129 | B1 | 12/2019 |

* cited by examiner (a) (b)

(a) (b)

(a) (b)

(a)

(b)

(a) (b)

(a) (b)

(a) (b)

SYSTEM INCLUDING SMART HOME MAT AND METHOD FOR CONTROLLING SAME

CROSS REFERENCE TO RELATED APPLICATIONS

This application is the National Phase of PCT International Application No. PCT/KR2022/003171, filed on Mar. 7, 2022, which is hereby expressly incorporated by reference into the present application.

TECHNICAL FIELD

The technical field of the present disclosure relates to a smart home mat. However, the technical concept of the present disclosure is applicable to all types of digital devices capable of contributing to an environment for exercising at home (for example, television (TV), smart home mat, wearable device (smart watch), and the like).

BACKGROUND

Due to the recent global outbreak of the coronavirus infection (COVID-19), there have been many restrictions on the movements of people.

Thus, people are incapable of freely going to the gymnasium and often have to wait for long periods to receive medical consultations or diagnoses at hospitals.

As a result, people are buying and using separate exercise equipment at home. However, the development of service platforms integrated with other devices has not been achieved. In particular, there is no real-time monitoring of the conditions of users to provide medical-related services.

DISCLOSURE

Technical Problem

One of the embodiments of the present disclosure aims to provide an integrated system that includes a television (TV), a smart home mat, a wearable device, and a server and a new service platform.

One of the embodiments of the present disclosure aims to provide meta home training capable of enabling virtual tracking and jogging using a smart home mat in conjunction with an avatar One of the embodiments of the present disclosure aims to provide digital healthcare services based on data obtained through a camera installed in a TV and a smart home mat.

One of the embodiments of the present disclosure aims to provide a responsive virtual avatar that changes in real-time based on information on exercise amounts of a user obtained through a smart home mat.

One of the embodiments of the present disclosure aims to provide a system capable of sharing a generated virtual avatar through a social networking service (SNS) and trading the avatar as a non-fungible token (NFT).

Technical Solution

Provided herein is a method of controlling a system having a communicable smart home mat according to an embodiment of the present disclosure. The method includes: capturing a user through a camera of a television (TV): generating a virtual avatar based on the captured image: outputting graphic images related to a virtual exercise environment to guide the user positioned on the smart home mat through a display of the TV; and controlling the graphic images related to the virtual exercise environment to be changed based on at least one of information on exercise amounts of the user or information on a health status of the user.

For example, the information on the exercise amounts of the user is determined based on at least one of a foot pressure or foot speed of the user recognized by the smart home mat.

For example, the smart home mat includes at least one of a cover film, a ground electrode, foam, adhesive tape, or a sensor pattern.

For example, hardness of the foam included in the smart home mat is automatically controlled according to a type of a ground surface included in the graphic images related to the virtual exercise environment.

For example, the system control method further includes: based on the virtual avatar is positioned on a first ground surface included in the graphic images related to the virtual exercise environment, changing the hardness of the foam to a minimum value (min); and based on the virtual avatar is positioned on a second ground surface included in the graphic images related to the virtual exercise environment, changing the hardness of the foam to a maximum value (max).

For example, the information on the health status of the user is determined based on at least one of a heart rate, a blood pressure, or a blood sugar recognized by a wearable device worn by the user.

For example, the system control method further includes: based on the information on the health status of the user corresponds to a first level, displaying a graphic image guiding the user to change an exercise speed on the smart home mat.

For example, the system control method further includes: based on the information on the health status of the user corresponds to a second level: displaying a graphic image guiding the user to stop exercise on the smart home mat; and sending an emergency call signal to a medical institution automatically.

For example, the system control method further includes: storing the information on the exercise amounts of the user performed on the smart home mat in a memory; and displaying levels of the physical changes of the user based on data stored in the memory.

For example, the system control method further includes: estimating an age group of the user positioned on the smart home mat through the camera of the TV: based on that the age group of the user falls within a first range, displaying extent of the physical changes by changing a body size of the virtual avatar; and based on that the age group of the user falls within a second range, displaying the extent of the physical changes by changing a color of a separate graphic image different from the virtual avatar.

Advantageous Effects

According to one of the embodiments of the present disclosure, an integrated system that includes a television (TV), a smart home mat, a wearable device, and a server and a new service platform may be provided.

According to one of the embodiments of the present disclosure, meta home training capable of enabling virtual tracking and jogging using a smart home mat in conjunction with an avatar may be provided.

According to one of the embodiments of the present disclosure, digital healthcare services based on data obtained through a camera installed in a TV and a smart home mat may be provided.

According to one of the embodiments of the present disclosure, a responsive virtual avatar that changes in real-time based on information on exercise amounts of a user obtained through a smart home mat may be provided.

According to one of the embodiments of the present disclosure, a system capable of sharing a generated virtual avatar through a social networking service (SNS) and trading the avatar as a non-fungible token (NFT) may be provided.

In addition to the various technical effects not explicitly mentioned above, the effects derived by those skilled in the art based on the details described in the specification and drawings may also be included within the scope of the present disclosure.

BEST MODE

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents, and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be directly connected with the other element or intervening elements may also be present. In contrast, when an element is referred to as being "directly connected with" another element, there are no intervening elements present.

A singular representation may include a plural representation unless it represents a definitely different meaning from the context.

Terms such as "include" or "has" are used herein and should be understood that they are intended to indicate an existence of several components, functions, or steps, disclosed in the specification, and it is also understood that greater or fewer components, functions, or steps may likewise be utilized.

Figure 1:
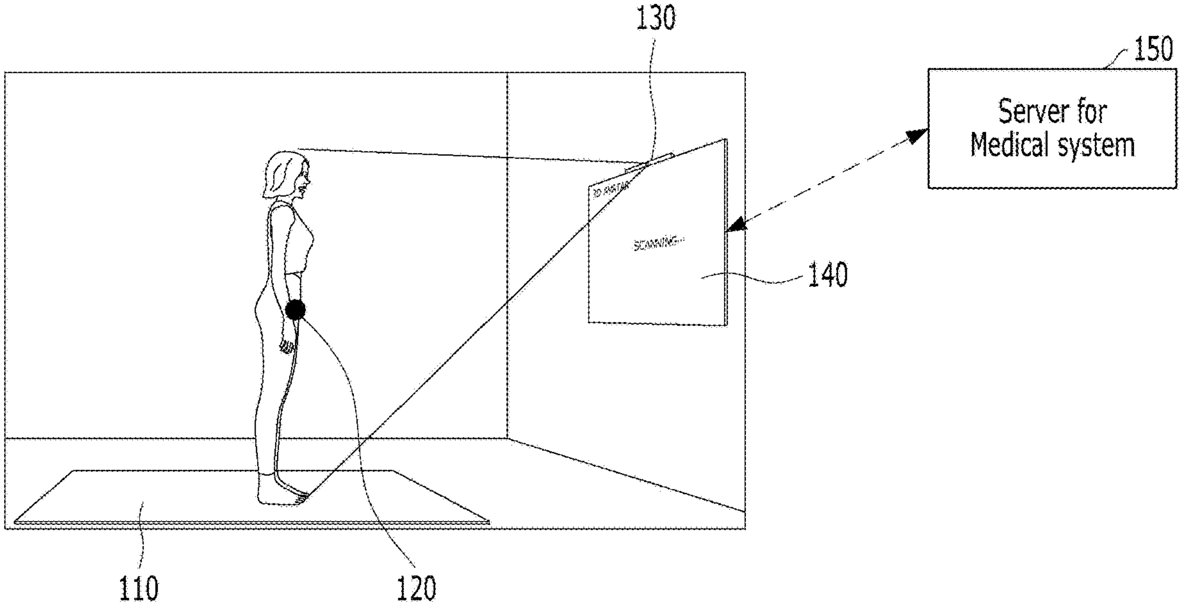
FIG. 1 is a diagram schematically illustrating an entire system according to one of the embodiments of the present disclosure.

FIG. 1 is a diagram schematically illustrating an entire system according to one of the embodiments of the present disclosure.

As shown in FIG. 1, the system according to an embodiment of the present disclosure includes a television (TV) 140, a smart home mat 110, a wearable device 120, and a server 150. However, considering the embodiments described throughout the specification and drawings, the present disclosure may be implemented with individual devices, and the scope of the present disclosure should be determined based on the appended claims.

According to an embodiment of the present disclosure, home training may be connected to preventive medicine to analyze data collected from a camera 130 installed in the TV 140 and various sensors (e.g., the wearable device 120) and provide personalized services.

The camera 130 installed in the TV 140 analyzes the body shape of a user and levels the results of strength, flexibility, and responsiveness tests. The smart home mat 110 may be designed to check the body balance of the user.

The wearable device 120 analyzes the heart rate, blood pressure, blood sugar, body fat, and other metrics of the user and transmits and receives related data to and from the server 150.

The TV 140 transmits and receives hospital health check-up medical data and remote diagnosis data through bidirectional communication with the server 150.

According to an embodiment of the present disclosure, various services may be provided through the smart home mat 110. For example, a meta home training system may be implemented in conjunction with an avatar performing virtual tracking/jogging.

As described above, the smart home mat 110 is introduced to address the issue of difficulty in exercising outdoors due to COVID-19. By wirelessly connecting the smart home mat 110 with the TV 140, the TV 140 displays synchronized visuals (e.g., live-action videos, games, 3D graphics, virtual avatars, etc.) that match the speed of the user walking or running on the smart home mat 110. Specifically, when using a virtual avatar, the face of the user is synthesized using the camera 130 attached to the TV 140.

According to an embodiment of the present disclosure, a digital healthcare service is provided using the smart home mat 110. The smart home mat 110 senses information on the amount of exercise such as the amount of walking or running done by the user and then displays the results through the TV 140. Additionally, the smart home mat 110 may analyze the body balancing of the user (e.g., the pressure difference between the left and right feet).

According to an embodiment of the present disclosure, a sensor fusion-based personalized digital healthcare service may additionally be provided using the camera 130 installed in the TV 140 and the smart home mat 110. The camera 130 senses analysis data on the body shape of the user, and the wearable device 120 senses data such as the heart rate, blood sugar, and blood pressure of the user. The resulting data is then transmitted to the server 150, thereby providing personalized remote medical consultations.

According to an embodiment of the present disclosure, a responsive avatar that interacts with the exercise analysis results of the user is newly proposed.

When the user is recognized through the camera 130 installed in the TV 140, it is designed to create a virtual avatar similar to the recognized user based on information on the facial image and body shape.

The face or body shape of the virtual avatar, which is automatically created, may also be modified according to a request from the user.

According to an embodiment of the present disclosure, after the creation of the virtual avatar, the body shape of the virtual avatar automatically changes in response to the exercise results of the user, instead of remaining fixed. For example, calorie consumption is calculated based on data sensed by the camera 130 and the smart home mat 110, and the size of the virtual avatar automatically decreases or increases through an analysis algorithm.

The virtual avatar may be shared with other users through a social networking service (SNS), and the original virtual avatar or the modified avatar may be traded as a non-fungible token (NFT).

In summary, the smart home mat 110 is equipped with communication functions, thereby co communicating with the TV 140, the server 150, and so on.

The camera 130 of the TV 140 captures a user, and the TV 140 generates a virtual avatar based on a captured image. A process of generating the virtual avatar will be described later with reference to FIG. 2.

The TV 140 displays graphic images related to a virtual exercise environment to guide the user who is positioned on the smart home mat 110.

The TV 140 is designed to control and modify the graphic images related to the virtual exercise environment based on at least one of information on the exercise amounts of the user or information on the health status of the user.

The information on the exercise amounts of the user is determined based on at least one of the pressure or speed of the user's feet recognized by the smart home mat 110. A related embodiment will be described in more detail later with reference to FIGS. 10 to 12.

The smart home mat includes, for example, at least one of a cover film, a ground electrode, foam, adhesive tape, or a sensor pattern. A related embodiment will be described in more detail later with reference to FIG. 13.

The information on the health status of the user is determined based on at least one of a heart rate, blood pressure, or blood sugar recognized by the wearable device 120 worn by the user.

If the information on the health status of the user exercising on the smart home mat 110 corresponds to a first level, the TV 140 displays a graphic image that guides the user to change the exercise speed thereof. A related embodiment will be described in more detail later with reference to FIG. 14.

If the information on the health status of the user exercising on the smart home mat 110 corresponds to a second level, the TV 140 displays a graphic image that guides the user to stop exercising on the smart home mat 110 and automatically sends an emergency call signal to the server 150 related to medical institutions. In this case, it is also possible to track the location of the user in need of emergency assistance through the IP address of the TV 140. A related embodiment will be described in more detail later with reference to FIG. 15.

Figure 2:
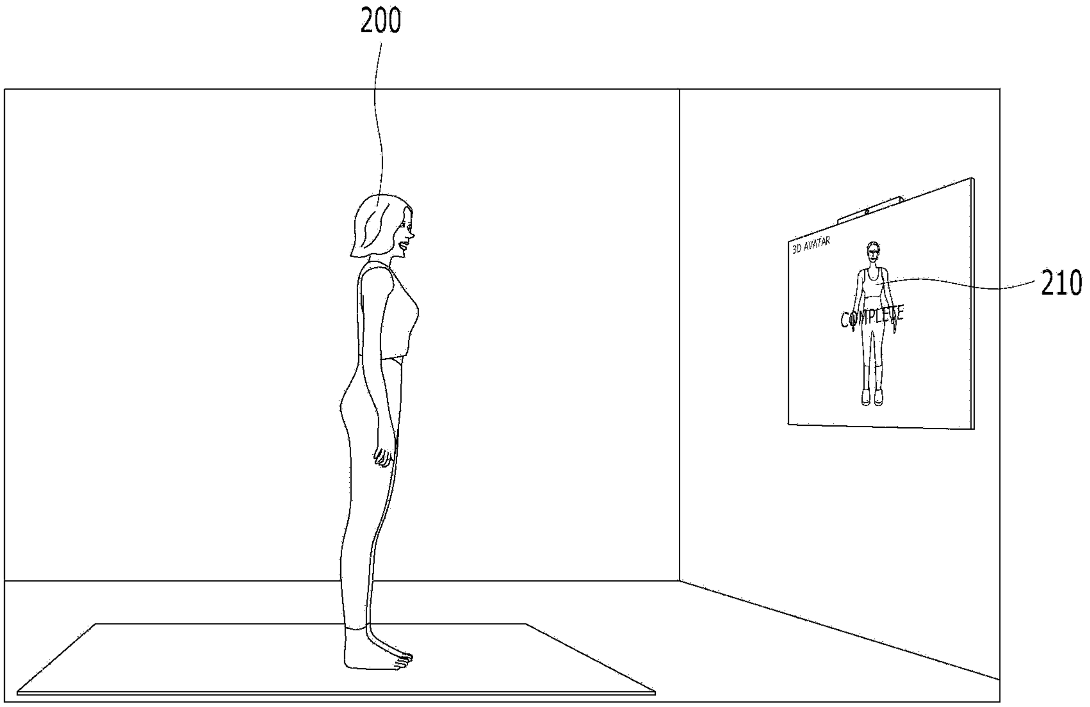
FIG. 2 is a diagram for explaining a process of generating a virtual avatar used in a home training service or healthcare service according to one of the embodiments of the present disclosure.

FIG. 2 is a diagram for explaining a process of generating a virtual avatar used in a home training service or healthcare service according to an embodiment of the present disclosure.

As shown in FIG. 2, the entire body of a user 200 is captured through a camera of a TV according to an embodiment of the present disclosure.

If the entire body of the user is not recognized by the camera, the TV according to the embodiment of the present disclosure additionally displays a message guiding the user to adjust the position of the user.

If the entire body of the user is recognized by the camera, the TV according to the embodiment of the present disclosure displays a virtual avatar 210.

The virtual avatar 210 corresponds to a graphic image similar to, for example, the face and body shape of the user 200.

The virtual avatar 210 created in this way may be used in both the home training service and healthcare service. However, the user may have needs to edit the virtual avatar generated by the TV. To this end, a solution will be described with reference to FIG. 3.

Figure 3:
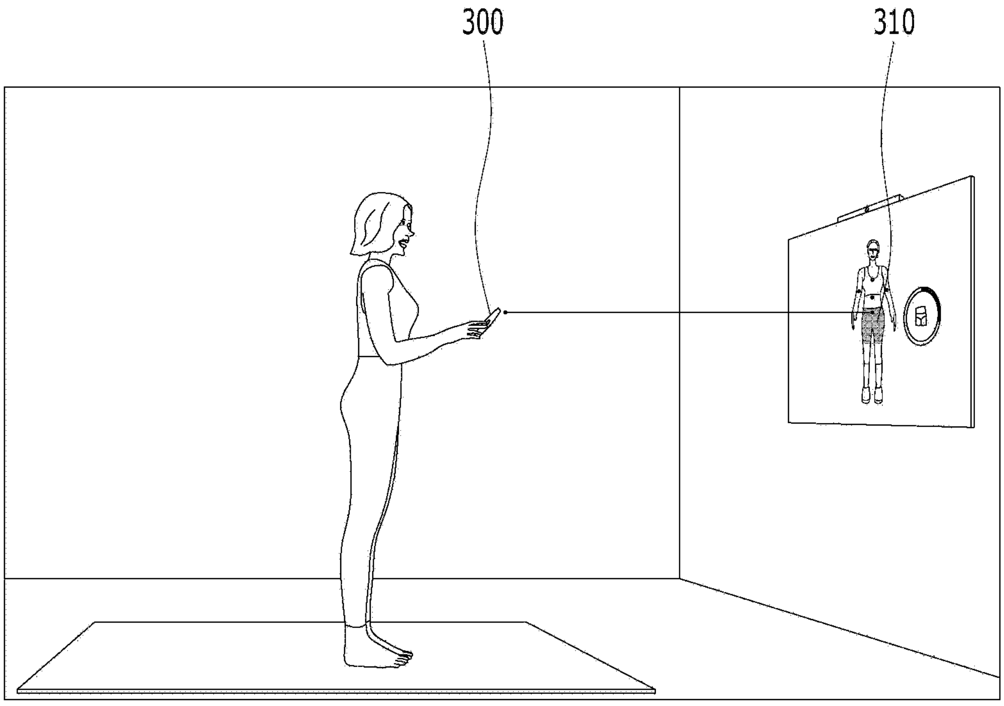
FIG. 3 is a diagram for explaining a process of editing the virtual avatar generated in FIG. 2.

FIG. 3 is a diagram for explaining a process of editing the virtual avatar generated in FIG. 2.

As shown in FIG. 3, according to an embodiment of the present disclosure, it is possible to edit only certain body parts of a virtual avatar 310 using a TV remote control 300.

Although not shown in FIG. 3, if a specific area to be edited is selected, exercise routines recommended for a particular body part may be automatically suggested.

Specifically, for example, if a user attempts to reduce the waist size of the virtual avatar, necessary exercise routines and amounts are calculated and displayed. Thus, the user has the advantage of being able to check in advance the exercise routines and amounts needed to achieve a physique similar to the edited virtual avatar (with a reduced waist size).

Figure 4:
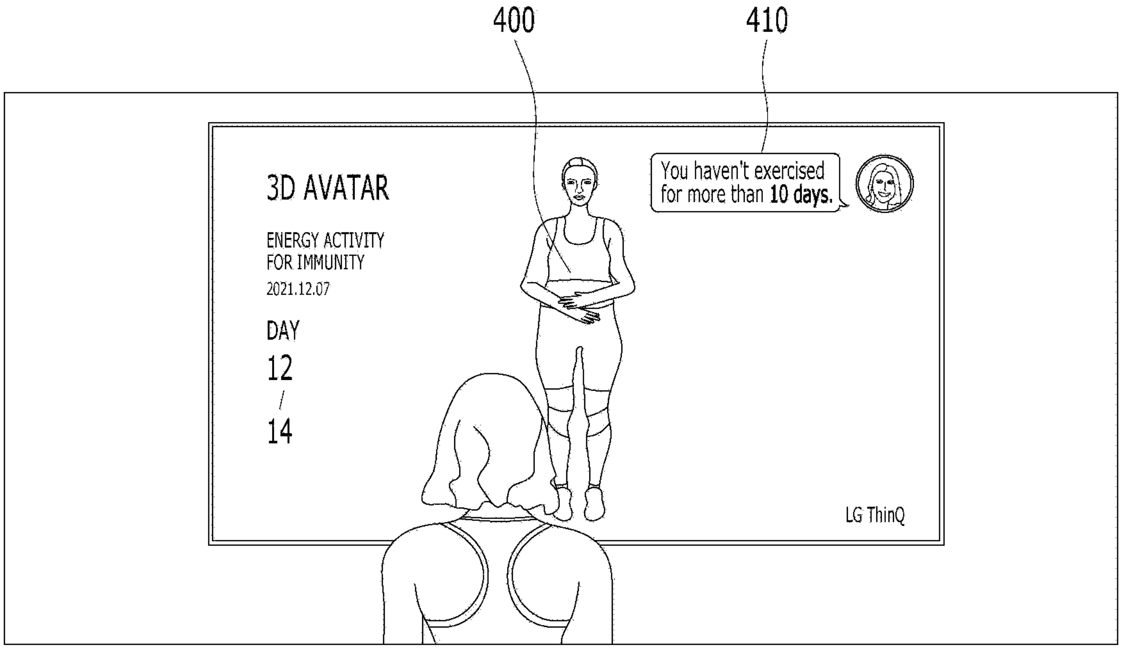
FIG. 4 is a diagram for explaining a process by which the graphic image of a virtual avatar is automatically updated based on communication results with a smart home mat.

FIG. 4 is a diagram for explaining a process by which the graphic image of a virtual avatar is automatically updated based on communication results with a smart home mat.

In contrast to the prior art, according to an embodiment of the present disclosure, the initially created virtual avatar is modified through interaction between the smart home mat and a TV.

For example, information on exercise amounts of a user sensed by the smart home mat is transmitted to the TV in real-time, and the TV stores the information in an internal memory or an external server.

If the user has not exercised on the smart home mat for more than 10 days, the number of days without exercise is displayed in a numerical format 410 as shown in FIG. 4.

However, to further encourage the user to exercise, the size 400 of the virtual avatar is designed to increase as shown in FIG. 4. The user has the advantage of being able to more intuitively and quickly recognize the need to exercise diligently.

Although not shown in FIG. 4, if the user exercises continuously for a predetermined period of time (e.g., 10 days), the size 400 of the avatar displayed in FIG. 4 is designed to return to the original size.

In addition, changes in the appearance of the avatar may be shared through an SNS, or the change history of the avatar may be configured to be transmitted via a preconfigured phone number, link, or SNS.

Figure 5:
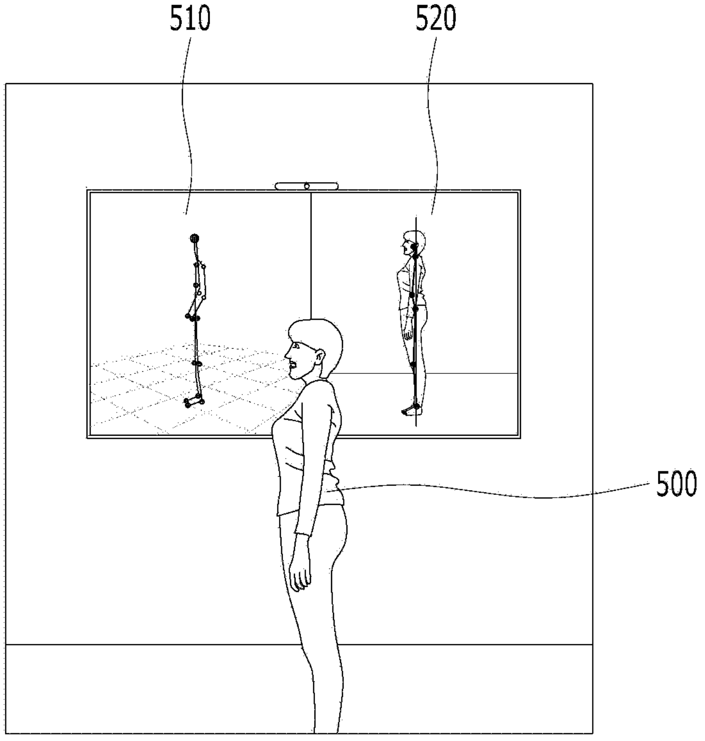
FIG. 5 is a diagram for explaining a process of providing two versions of the appearance of a user before the user exercises using a smart home mat according to one of the embodiments of the present disclosure.

FIG. 5 is a diagram for explaining a process of providing two versions of the appearance of a user before the user exercises using a smart home mat according to an embodiment of the present disclosure.

As shown in FIG. 5, the appearance of a user 500 before exercise is captured using a camera of a TV and displayed based on a skeleton pose recognition technology.

As shown in FIG. 5, it is possible to display both a skeleton image 510 and an actual photograph 520 of the user or only one of the skeleton image 510 and actual photograph 520 according to the preference of the user.

Based on the analysis of the skeleton image 510, a TV according to an embodiment of the present disclosure provides feedback on the analysis results of the body shape. For example, the TV may show an enlarged view of abnormal body parts or display customized exercise content.

Figure 6:
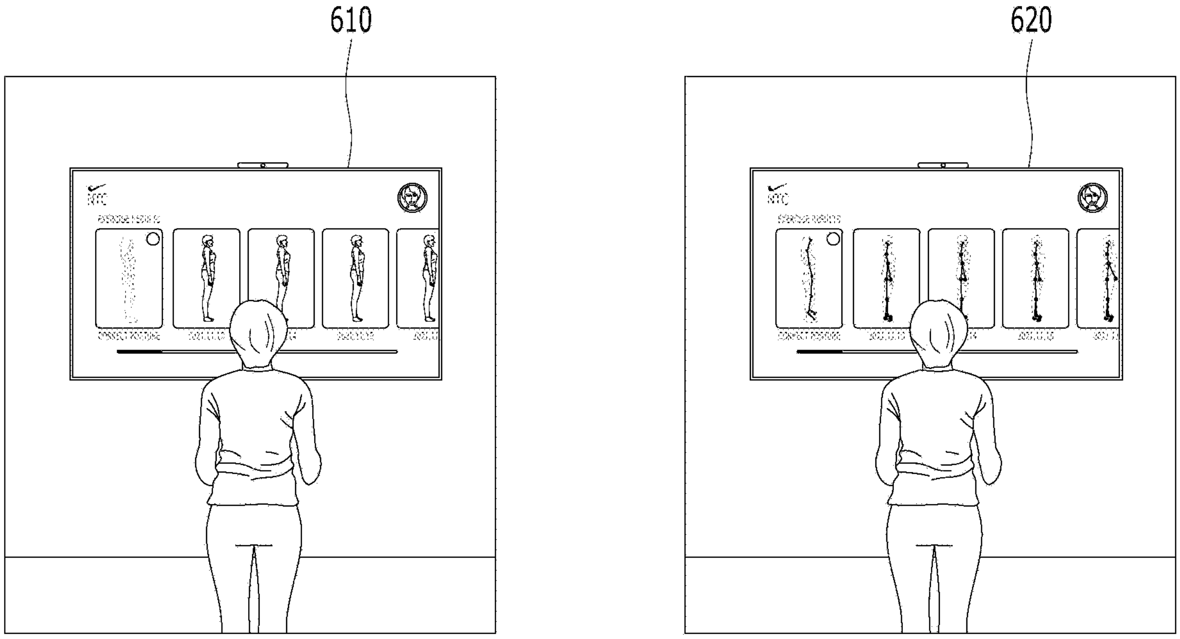
FIG. 6 is a diagram for explaining a process of providing two versions of the appearance of a user after the user exercises using a smart home mat according to one of the embodiments of the present disclosure.

FIG. 6 is a diagram for explaining a process of providing two versions of the appearance of a user after the user exercises using a smart home mat according to an embodiment of the present disclosure.

As shown in FIG. 5, it is assumed that the user has completed recording using before exercising using the smart home mat. However, the recording is designed to be performed each time the user starts exercising. Such a design has the advantage of allowing more accurate tracking of physical changes of the user over time due to exercise.

For example, the physical changes of the user may be displayed based on an actual photo 610 as shown in FIG. 6(*a*). Alternatively, the physical changes of the user may be displayed based on a skeleton image 620 as shown in FIG. 6(*b*).

Figure 7:
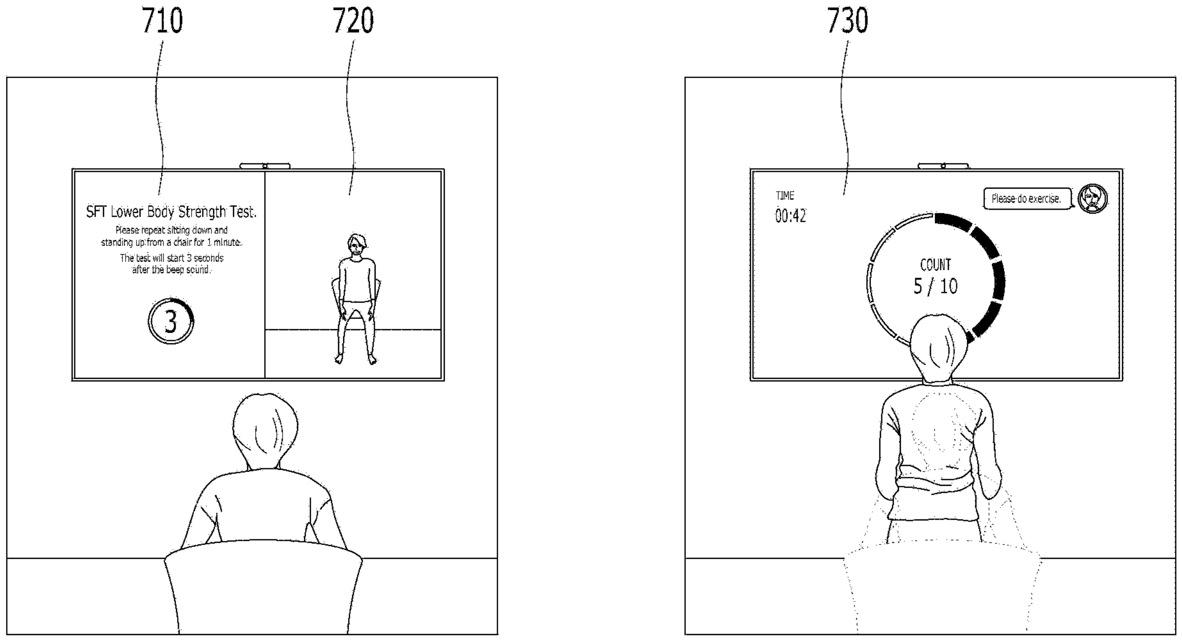
FIG. 7 is a diagram for explaining a television (TV) screen that guides a user to exercise according to one of the embodiments of the present disclosure.

FIG. 7 is a diagram for explaining a TV screen that guides a user to exercise according to an embodiment of the present disclosure.

As shown in FIG. 7(*a*), a message 710 that guides the user to exercise and information 720 on a required pose may be displayed together. The movements of the user are analyzed through a TV camera, and the TV screen is changed to a screen 730 that shows an increasing number each time the user successfully completes the required exercise as shown in FIG. 7(*b*).

That is, it is also possible to provide a self-diagnosis program for health status by age in addition to simply guiding the user to exercise.

For example, after analyzing the exercise movements of the user in front of the TV using the camera installed in the TV, individual physical abilities (e.g., responsiveness, strength, flexibility, etc.) are stored in a database and, if necessary, transmitted to a medical-related server.

Figure 8:
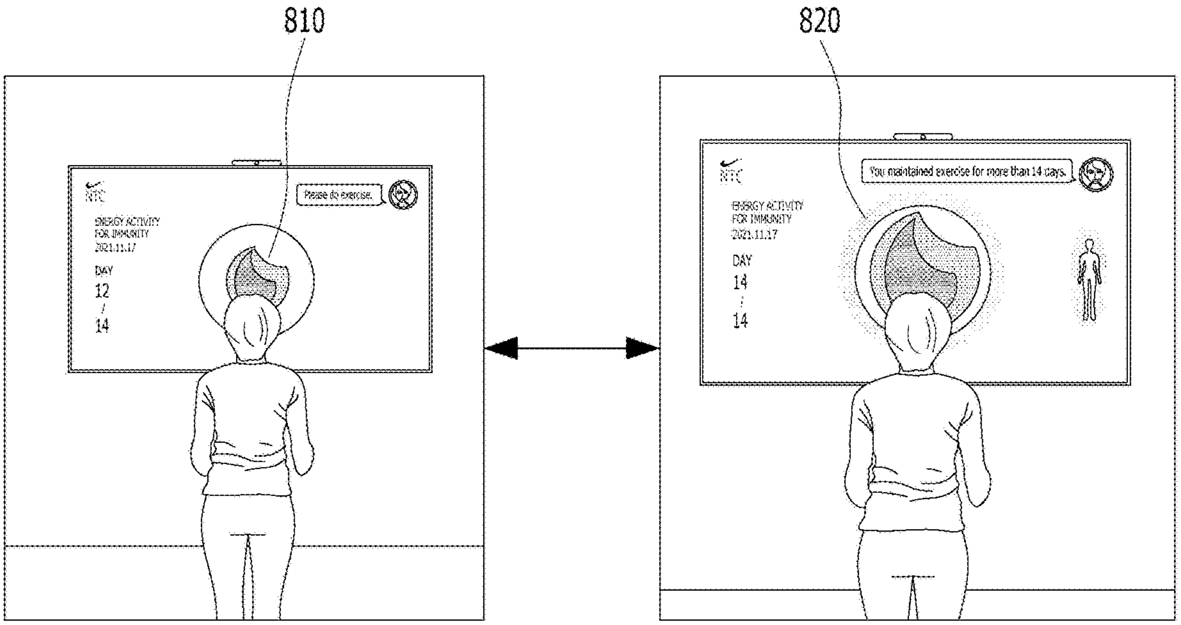
FIG. 8 is a diagram illustrating monitoring results of an exercise history of a user according to one of the embodiments of the present disclosure.

FIG. 8 is a diagram illustrating monitoring results of an exercise history of a user according to an embodiment of the present disclosure.

As described above, when the user exercises using a smart home mat, the TV accumulates and calculates exercise amounts of the user through real-time communication with the smart home mat. It is important for the TV to provide appropriate feedback to the user to help the user to continue exercising without interruption.

The TV according to an embodiment of the present disclosure stores information on the exercise amounts of the user in a memory through communication with the smart home mat, and displays the levels of physical changes of the user based on the data stored in the memory.

In particular, according to an embodiment of the present disclosure, the TV estimates the age group of the user by analyzing images obtained through the camera.

If it is determined that the age group of the user falls within a first range (e.g., young adults under 50), the TV displays the extent of physical changes according to the exercise amounts by changing the body size of a virtual avatar corresponding to the user (e.g., 400 shown in FIG. 4).

On the other hand, if it is determined that the age group of the user falls within a second range (e.g., seniors over 60), the extent of physical changes according to the exercise amounts is displayed by changing the color of a separate graphic image (e.g., circular shape 810 or 820 shown in FIG. 8), different from the virtual avatar.

In other words, according to an embodiment of the present disclosure, the exercise participation time (or the number of days) is linked to a virtual immunity symbol (energy activity for immunity), thereby guiding home training more efficiently and naturally. The shape and color of the symbol 810 or 820 shown in FIG. 8 may be changed by the user.

If the user does not exercise using the smart home mat, a virtual ball symbolizing immunity becomes smaller as shown in FIG. 8(*a*). When the user resumes exercising, the virtual ball 810 gradually grows larger.

For example, if the user exercises for 14 consecutive days using the smart home mat, the virtual ball 820 gradually grows larger and is additionally highlighted as shown in FIG. 8(*b*).

Figure 9:
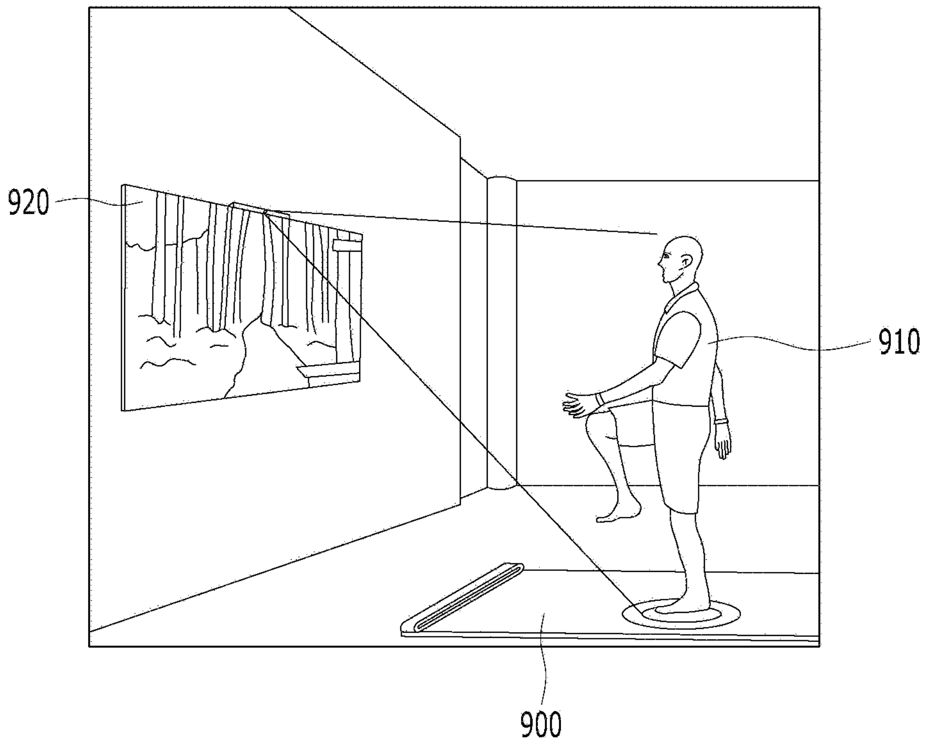
FIG. 9 is a diagram for explaining a process of using a smart home mat according to one of the embodiments of the present disclosure.

FIG. 9 is a diagram for explaining a process of using a smart home mat according to an embodiment of the present disclosure.

According to an embodiment of the present disclosure, the background screen of a TV 920 automatically changes in synchronization with exercise amounts of a user 910 such as the amount of jogging/walking performed by the user 910 on a smart home mat 900.

First, the TV 920 displays graphic images related to a virtual exercise environment.

The hardness of the foam included in the smart home mat 900 is automatically controlled according to the type of a ground surface included in the graphic images of the virtual exercise environment displayed on the TV 920.

Although not shown in FIG. 9, it is assumed that a virtual avatar is positioned on a first ground surface included in the graphic images of the virtual exercise environment.

Here, the first ground surface may be, for example, soil of the mountain such as a trail path.

In this case, by changing the hardness of the foam in the smart home mat 900 to a minimum value (min), the user 910 may feel as if the user is exercising in a natural environment corresponding to the virtual exercise environment displayed on the TV 920.

On the other hand, it is assumed that the virtual avatar is positioned on a second ground surface included in the graphic images of the virtual exercise environment.

Here, the second ground surface may be, for example a city sidewalk such as asphalt.

In this case, by changing the hardness of the foam in the smart home mat 900 to a maximum value (max), the user 910 may feel as if the user is exercising in an urban environment corresponding to the virtual exercise environment displayed on the TV 920.

The main components and functions of the smart home mat described above will be further detailed later with reference to FIGS. 10 to 13.

Figure 10:
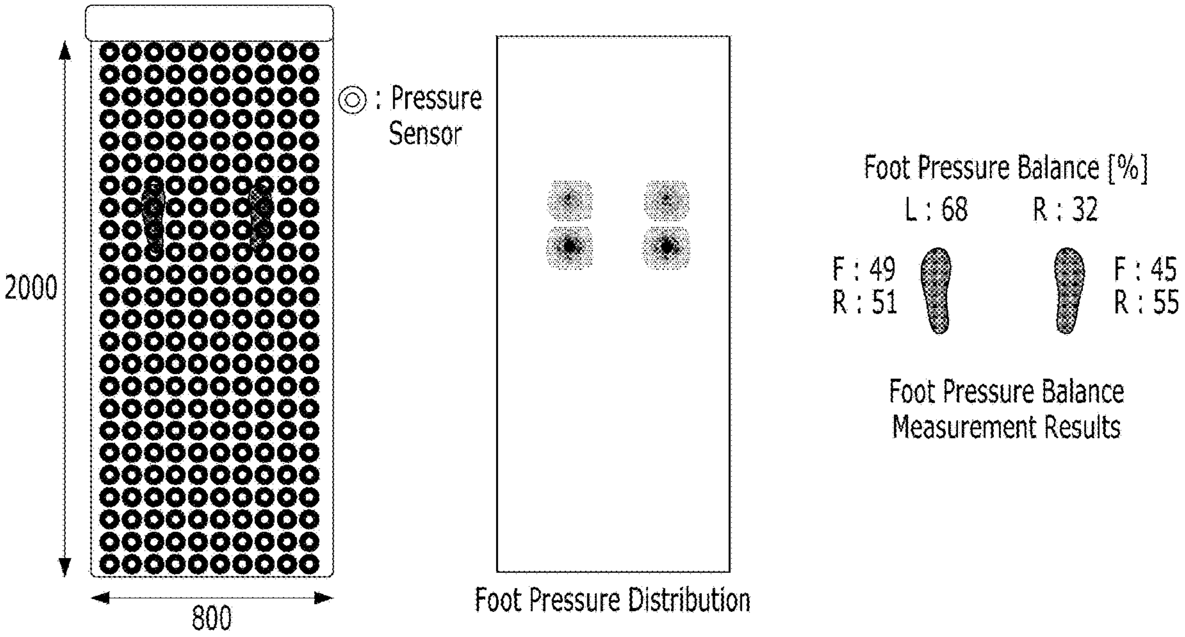
FIG. 10 is a diagram for explaining pressure sensors mounted on a smart home mat according to one of the embodiments of the present disclosure.

FIG. 10 is a diagram for explaining pressure sensors mounted on a smart home mat according to an embodiment of the present disclosure.

As shown in FIG. 10(*a*), the smart home mat according to an embodiment of the present disclosure is, for example, configured with a width of 800 millimeter (mm) and a length of 2000 mm and is equipped with dozens or hundreds of pressure sensors designed to detect the foot pressure distribution of a user.

In addition, as shown in FIG. 10(*b*), the pressure sensors may measure the pressure balance between the left and right feet for each user and also determine whether more pressure is applied to the front or back of each foot.

According to the present disclosure, such data may be collected, thereby guiding the user to achieve better balance between the left and right feet as well as the front and back parts of the feet while walking or running.

Figure 11:
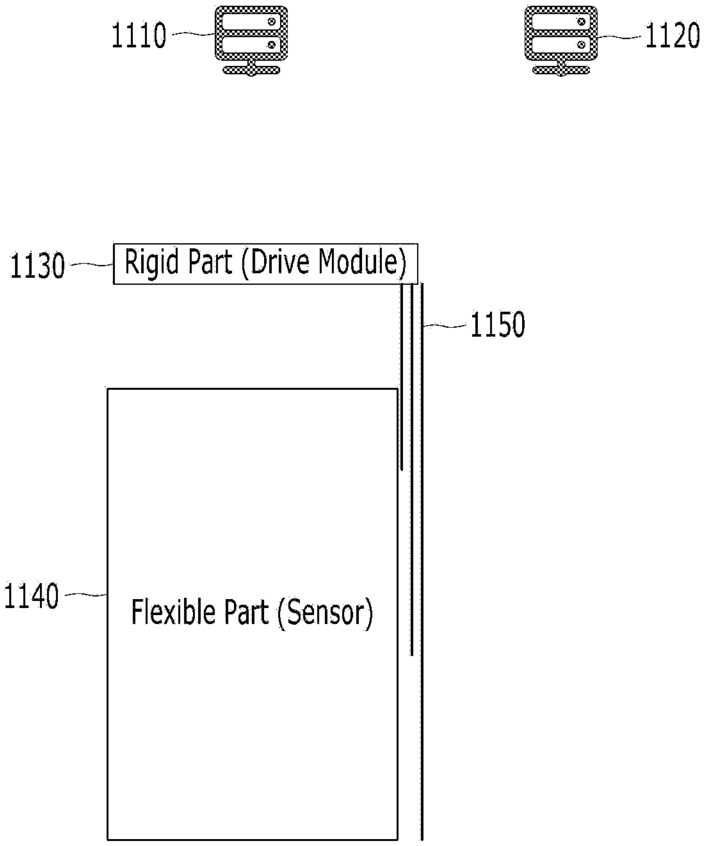
FIG. 11 is a diagram for explaining a process for a smart home mat to communicate with other servers according to one of the embodiments of the present disclosure.

FIG. 11 is a diagram for explaining a process for a smart home mat to communicate with other servers according to an embodiment of the present disclosure.

The smart home mat according to an embodiment of the present disclosure includes a drive module 1130, a flexible part 1140, and wires 1150. Data detected by the flexible part 1140 is transmitted to the drive module 1130 via the wires 1150, and the drive module 1130 is additionally equipped with communication functions.

Therefore, the drive module 1130 transmits the data received from the flexible part 1140 to a first server 1110 and a second server 1120. In this case, the first server 1110 may correspond to a server for analyzing the posture of a user, and the second server 1120 may correspond to a server related to medical institutions.

For example, the overall size of the smart home mat is implemented as 1806×750×15 mm, the drive module 1130 included in the smart home mat is implemented as 100×750×15 mm, and the flexible part 1140 is implemented as 1706×750×10 mm.

In addition, the number of sensors included in the flexible part 1140 is, for example, 240 (channels), and a pressure range capable of being sensed is 0.6 to 2 kg/cm$^2$.

The transmission interval of the sensed data is determined to be, for example, 100 milliseconds (ms). However, the scope of the present disclosure is not limited to the aforementioned values.

Although not shown in FIG. 11, the smart home mat according to the embodiment of the present disclosure is paired with a TV and transmits and receives various types of data to and from the TV as described above.

Figure 12:
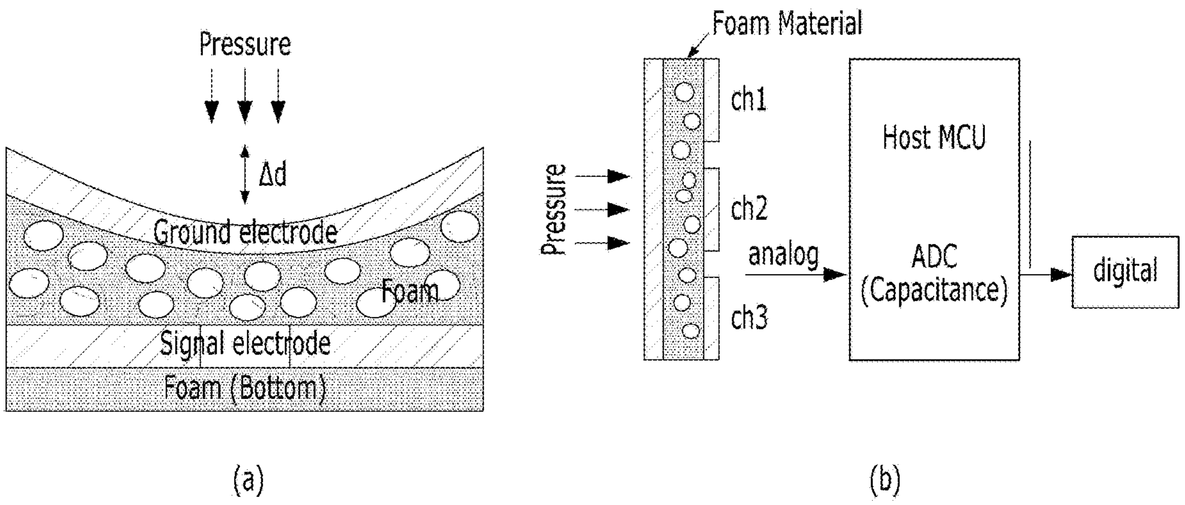
FIG. 12 is a diagram for explaining a process by which a smart home mat calculates the pressure of a user according to one of the embodiments of the present disclosure.

FIG. 12 is a diagram for explaining a process by which a smart home mat calculates the pressure of a user according to one of the embodiments of the present disclosure.

As shown in FIG. 12(*a*), when the pressure is applied as the user moves on the smart home mat, changes in capacitance occur due to the material deformation (deformation between electrodes) of the smart home mat. In this case, the capacitance value is calculated by Equation 1.

$$C = \varepsilon * (A/d) \quad \text{[Equation 1]}$$

In Equation 1, C represents capacitance, ε represents a dielectric constant, and A represents an area.

The calculated capacitance value is input to a microcontroller unit (MCU) for each channel (sensor), and the MCU converts the value into a digital signal. The MCU aggregates all data and transmits the aggregated data to a controller (e.g., located in a TV).

The controller converts the value for each channel transmitted from the MCU into a pressure using a premeasured calibration curve for each channel.

Figure 13:
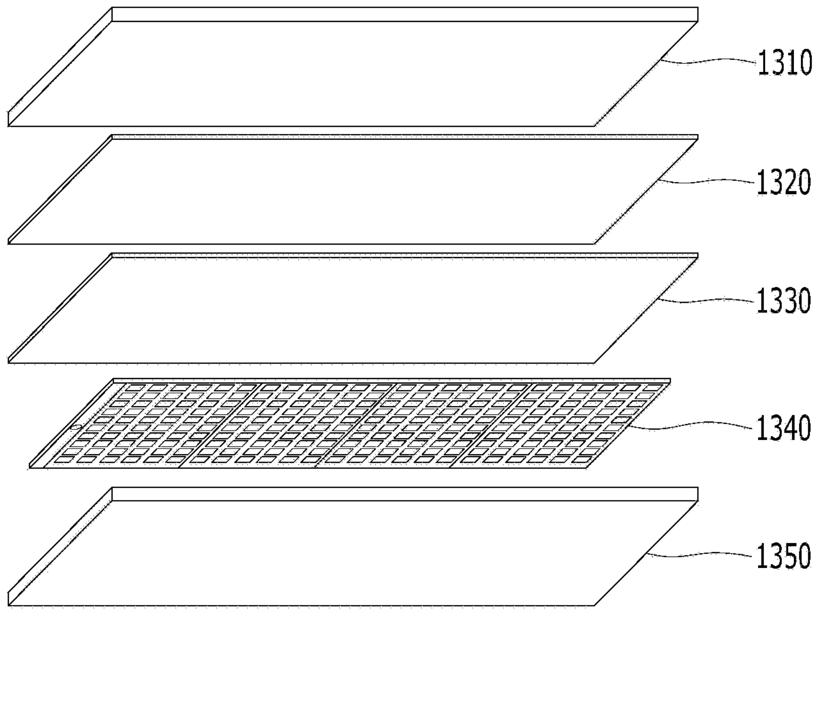
FIG. 13 is a diagram for explaining a plurality of layers included in a smart home mat according to one of the embodiments of the present disclosure.

FIG. 13 is a diagram for explaining a plurality of layers that make up a smart home mat according to an embodiment of the present disclosure.

As shown in FIG. 13, the smart home mat according to the embodiment of the present disclosure is implemented with a multi-layer structure capable of multi-channel sensing to protect sensors.

A first layer 1310 corresponds to a top cover film and is designed to protect the sensors. For example, the aforementioned first layer 1310 is made of a thermoplastic elastomer (TPE), and the thickness thereof is implemented to be approximately 8 mm.

A second layer 1320 corresponds to foam and is used to measure changes in the distance between ground and signal electrodes due to deformation from the foot pressure of the user. The thickness of the aforementioned second layer 1320 is implemented to be approximately 1 mm.

A third layer 1330 corresponds to adhesive tape and acts as an adhesive layer. For example, the aforementioned third layer 1330 is made of acrylic, and the thickness thereof is implemented to be approximately 0.05 mm.

A fourth layer 1340 corresponds to a sensor pattern and is implemented as a flexible printed circuit board (FPCB). The thickness thereof is implemented to be approximately 0.1 mm.

A fifth layer 1350 corresponds to a bottom cover film and is designed to protect the sensors. For example, the aforementioned fifth layer 1350 is made of a TPE, and the thickness thereof is implemented to be approximately 8 mm.

Although not shown in FIG. 13, the ground electrode is added between the first layer 1310 and the second layer 1320 to enable external interference shielding. The thickness of the ground electrode is implemented to be approximately 0.1 mm.

Figure 14:
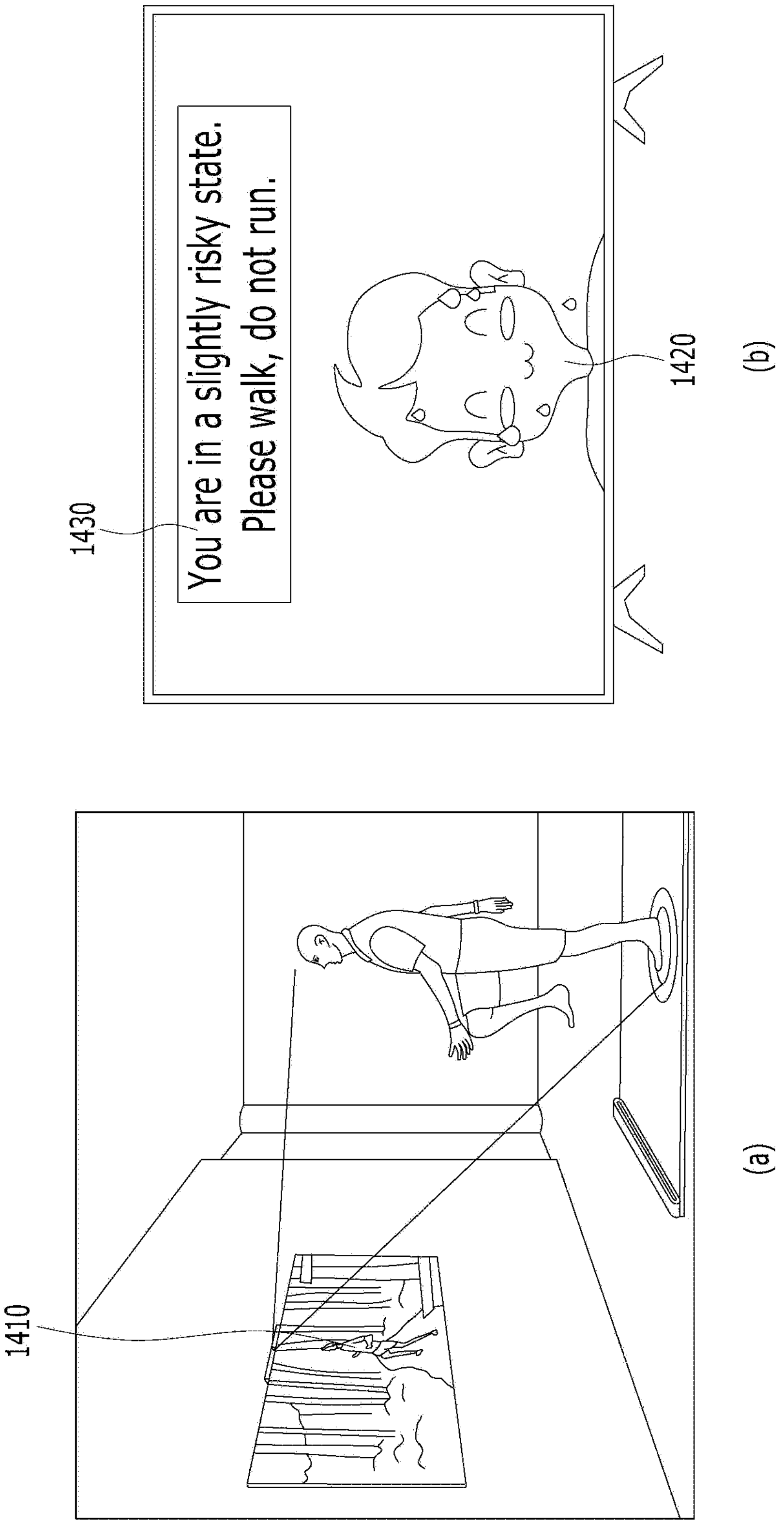
FIG. 14 is a diagram for explaining a solution when information on the health status of a user exercising on a smart home mat corresponds to a first level according to one of the embodiments of the present disclosure.

FIG. 14 is a diagram for explaining a solution when information on the health status of a user exercising on a smart home mat corresponds to a first level according to one of the embodiments of the present disclosure.

As shown in FIG. 14(*a*), when the user is recognized on the smart home mat or when there is a request from the user, a virtual exercise environment and a virtual avatar 1410 are displayed on a TV screen.

As described above, the health status of the user may be periodically or continuously monitored through a wearable device (120 shown in FIG. 1) worn by the user.

In this case, if the monitored health status of the user corresponds to the first level, for example, if the average heart rate of the user is 50 to 60 beats per minute and the heart rate increases by more than 30%, that is, if the heart rate is detected as 65 to 78 beats per minute, the health status is considered as the first level (slightly risky). Although the heart rate is used as an example, measuring the risk level based on information on a blood pressure or blood sugar also falls within the scope of the present disclosure.

Thereafter, a struggling virtual avatar 1420 is displayed along with a warning message 1430 as shown in FIG. 14(*b*). Thus, the user may recognize the risk status more intuitively and quickly compared to simply displaying the heart rate.

Figure 15:
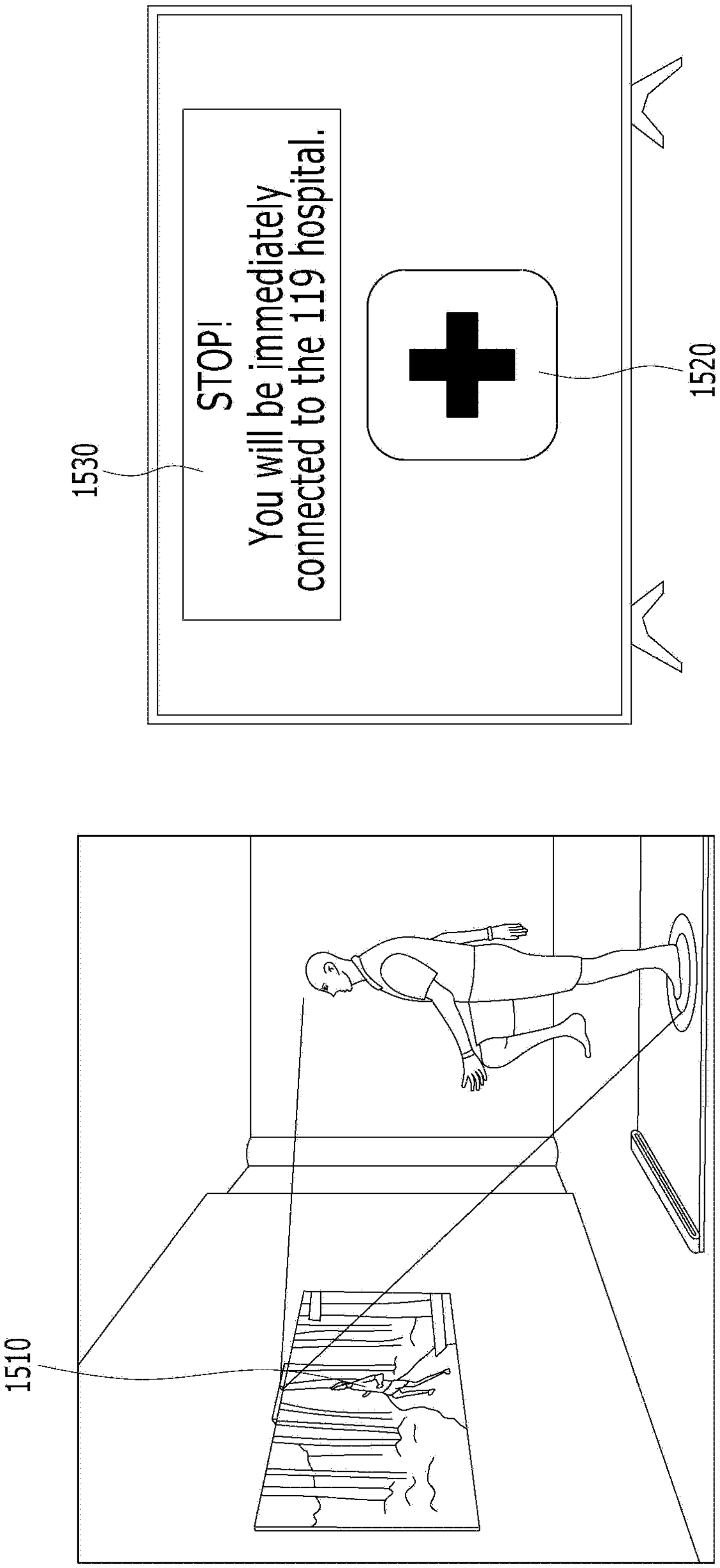
FIG. 15 is a diagram for explaining a solution when information on the health status of a user exercising on a smart home mat corresponds to a second level according to one of the embodiments of the present disclosure.

FIG. 15 is a diagram for explaining a solution when information on the health status of a user exercising on a smart home mat corresponds to a second level according to one of the embodiments of the present disclosure. It is assumed that the health status of the user during exercise is more dangerous compared to that described in FIG. 14.

As shown in FIG. 15(*a*), when the user is recognized on the smart home mat or when there is a request from the user, a virtual exercise environment and a virtual avatar 1510 are displayed on a TV screen.

As described above, the health status of the user may be periodically or continuously monitored through a wearable device (120 shown in FIG. 1) worn by the user.

In this case, if the monitored health status of the user corresponds to the second level, for example, if the average heart rate of the user is 50 to 60 beats per minute and the heart rate increases by more than 50%, that is, if the heart rate is detected as 75 to 80 beats per minute, the health status is considered as the second level (significantly risky). Although the heart rate is used as an example, measuring the risk level based on information on a blood pressure or blood sugar also falls within the scope of the present disclosure.

Subsequently, as shown in FIG. 15(*b*), a hospital logo 1520 is displayed along with a warning message 1530 to stop exercising immediately, instead of the virtual avatar. Additionally, an automatic call signal is transmitted to an emergency center such as a hospital. In this case, according to the present disclosure, the emergency center is allowed to automatically recognize the location of the user exercising on the smart home mat through the IP network address of the TV.

Figure 16:
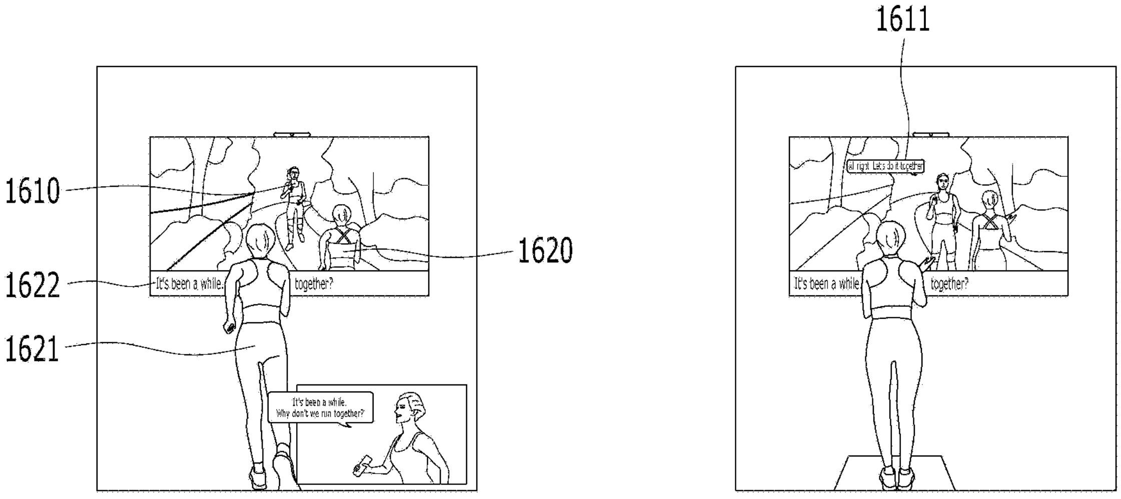
FIG. 16 is a diagram for explaining a process of providing a chat service during home training according to one of the embodiments of the present disclosure.

FIG. 16 is a diagram for explaining a process of providing a chat service during home training according to one of the embodiments of the present disclosure. Hereinafter, a solution for implementing metaverse chat home training will be described with reference to FIG. 16.

First, it is assumed that a user 1621 shown in FIG. 16(*a*) is exercising on the aforementioned smart home mat. In addition, the user 1621 may select a virtual exercise course (or an actual location). For example, the exercise course could be a road in a specific area of LA, a road in Seoul, or a trail in Jeju Island.

In this case, the user 1621 sends a message encouraging another user (e.g., acquaintance) to exercise on the same virtual course through a mobile phone, TV, or social media. Thus, while exercising on the virtual course, the user meets a virtual avatar 1610 of the other use who is also exercising on the same virtual course at a certain point.

When the user 1621 speaks any words, the same content is displayed on a TV screen in the form of subtitles 1622 as if an avatar 1620 corresponding to the user is speaking.

In addition, as shown in FIG. 16(*b*), the content spoken by the avatar 1611 of the other user is also displayed around the avatar 1611.

For example, a mother in Korea may exercise at home and invite her daughter, who lives in the United States, in real time to exercise together in a virtual space and chat with each other.

Figure 17:
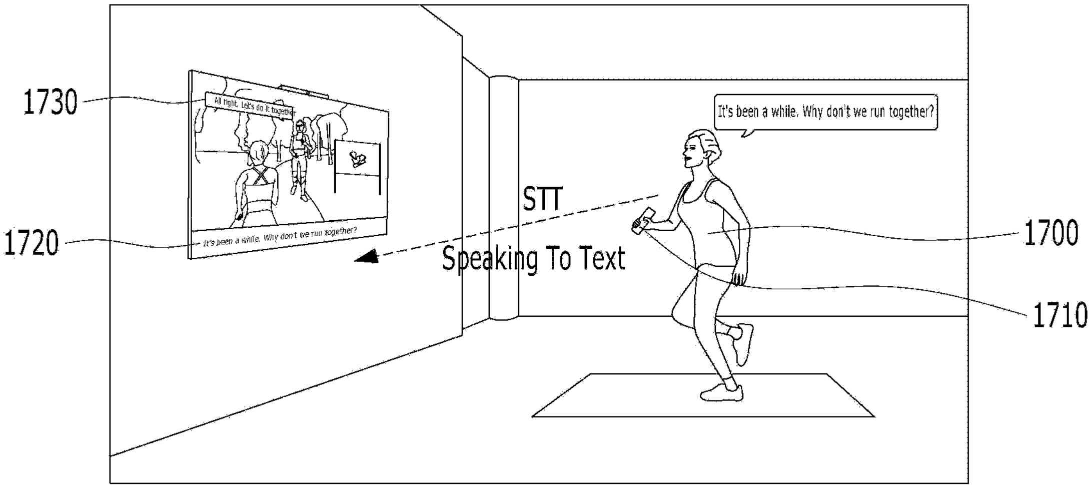
FIG. 17 is a diagram for explaining devices necessary for implementing FIG. 16.

FIG. 17 is a diagram for explaining devices necessary for implementing FIG. 16. In FIG. 16, it is explained that the content spoken by a user could be displayed on a TV screen in the form of subtitles. The devices necessary for the implementation will be described in more detail with reference to FIG. 17.

As shown in FIG. 17, it is assumed that a user 1700 is exercising on the aforementioned smart home mat. To implement the speech to text (STT) function, the user 1700 exercises while equipped with a TV remote control 1710.

When the user 1700 speaks, audio data recognized through a microphone of the TV remote control 1710 is transmitted to a TV. The TV is designed to convert the received audio data into text and display the text at the bottom of a screen 1720.

In addition, content 1730 spoken by another avatar 1730 encountered in a virtual space is also designed to be displayed together.

In particular, considering that pressing a specific button each time to activate the microphone function on the TV remote control during exercise may be burdensome for the user, a solution to this issue is proposed as one of the features of the present disclosure.

For example, when a virtual avatar corresponding to a specific acquaintance configured by the user 1700 is recognized on a TV screen, the microphone function and STT function of the TV remote control 1710 are automatically activated. Therefore, unnecessary audio is not recognized and there is no need to press a separate button to activate the voice recognition function while the user 1700 is exercising, thereby allowing the user 1700 to focus more on exercise and conversation with another person.

FIG. 17 shows that conversation with another avatar is conducted only in the form of text chat. However, designing that the voice of another person is directly output through a TV speaker also falls within the scope of the present disclosure.

Figure 18:
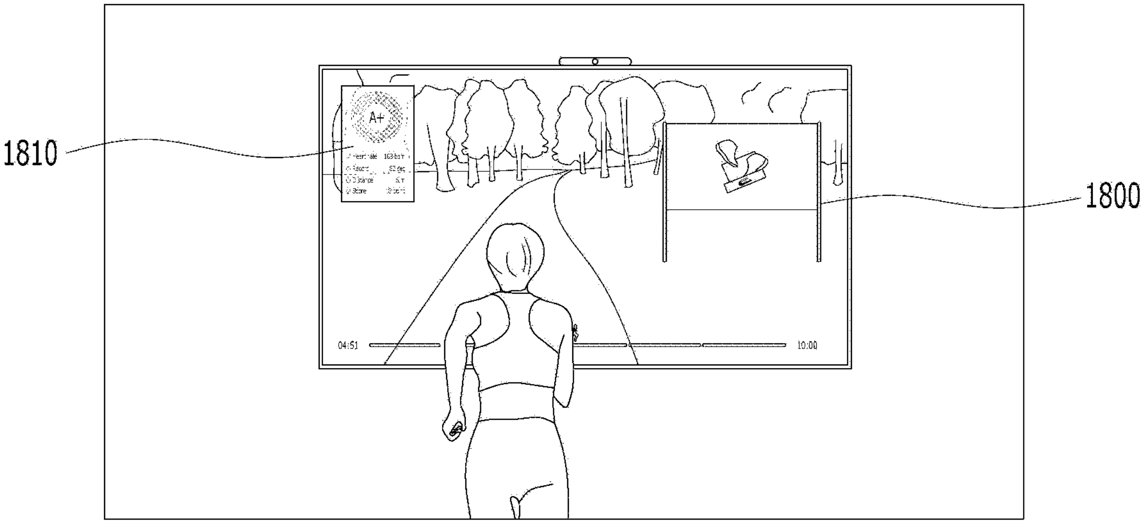
FIG. 18 is a diagram for explaining a process of providing additional services during home training according to one of the embodiments of the present disclosure.

FIG. 18 is a diagram for explaining a process of providing additional services during home training according to one of the embodiments of the present disclosure.

As shown in FIG. 18, during home training, information on the exercise guide or current exercise status for the user is displayed in a first area 1810, and information on a virtual billboard is displayed in a second area 1800. By enabling transactions for the virtual billboard, content related to virtual walking paths may be further enhanced.

Figure 19:
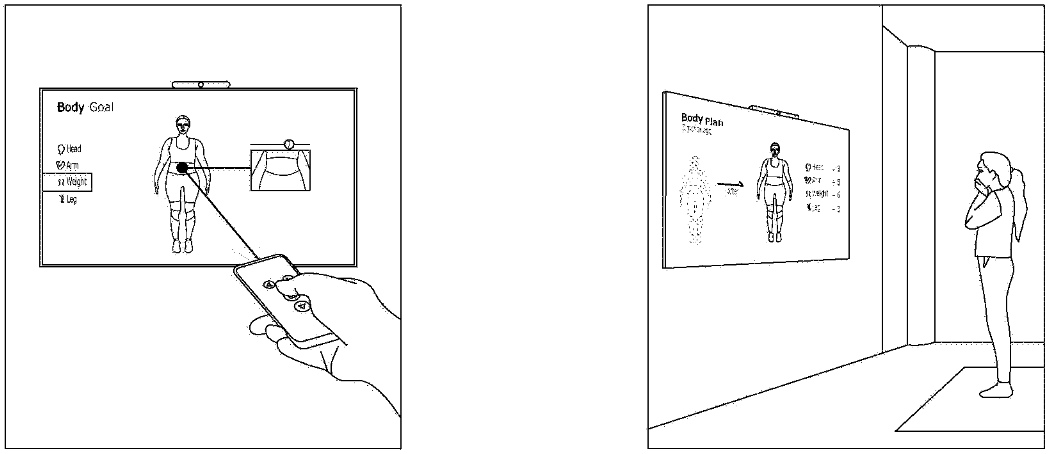
FIG. 19 is a diagram for explaining a process of generating a responsive virtual avatar according to one of the embodiments of the present disclosure.

FIG. 19 is a diagram for explaining a process of generating a responsive virtual avatar according to one of the embodiments of the present disclosure.

First, as shown in FIG. 19(*a*), an option is provided to edit some body parts (e.g., forearms, thighs, abdomen, etc.) of a virtual avatar similar to the current body shape of a user. In addition, the system is designed to display customized exercise content necessary to achieve the edited avatar (e.g., the waist circumference is changed from 30 inches to 25 inches).

Data related to the exercise history of the user is recognized through a smart home mat and transmitted to a TV. If the user does not exercise on the smart home mat for a predetermined period of time (e.g., more than a week), the virtual avatar is designed to also transform to a fatter appearance as shown in FIG. 19(*b*).

Thus, the appearance of the virtual avatar automatically changes in proportion to the actual exercise of the user. The virtual avatar may be registered and traded as an NFT, thereby further activating related services.

Figure 20:
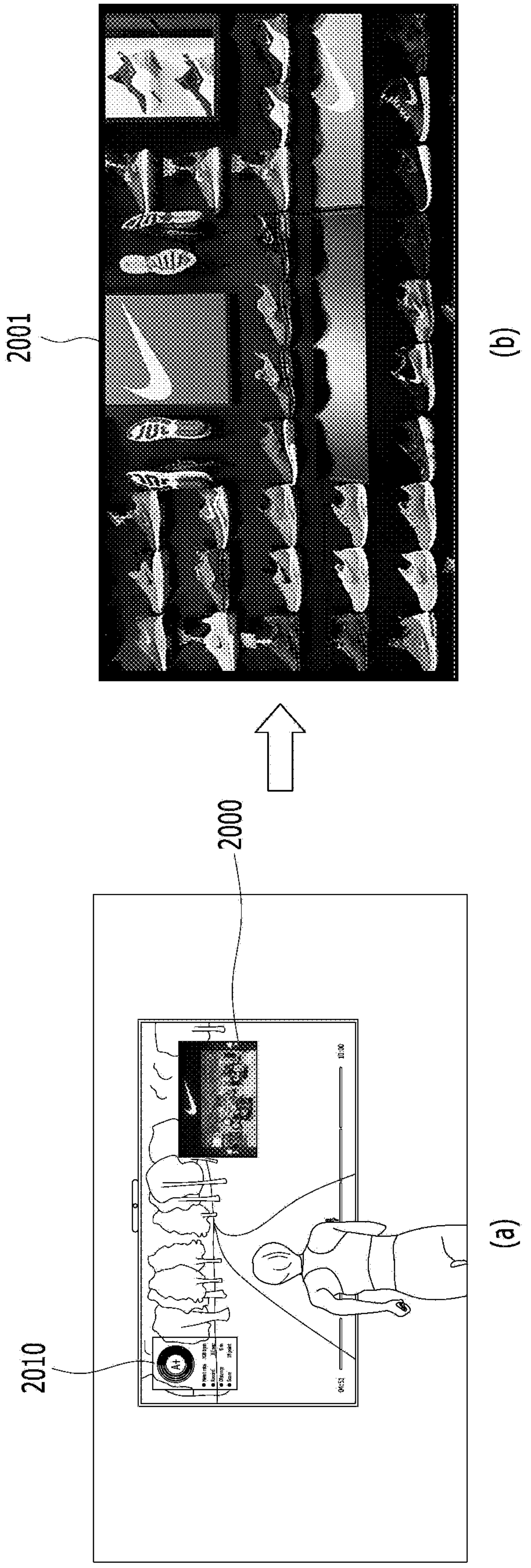
FIG. 20 is a diagram for explaining a process of purchasing a specific item during home training according to one of the embodiments of the present disclosure.

FIG. 20 is a diagram for explaining a process of purchasing a specific item during home training according to one of the embodiments of the present disclosure.

In the previous embodiments, methods of allowing a user to experience virtual tracking or virtual jogging using a smart home mat and a TV have been described. However, according to another embodiment of the present disclosure, while the virtual tracking or virtual jogging service is being provided, the TV is designed to display user health information 2010 in a first area and a virtual billboard or virtual store 2000 in a second area as shown in FIG. 20(*a*). It is understood by those skilled in the art that designing the first and second areas to be switchable with each other or displaying additional information in only one of the areas falls within the scope of the present disclosure.

In particular, from the perspective of a service provider, additional revenue may be expected through the sale or rental of the virtual billboard or virtual store 2000 displayed in the aforementioned second area.

More specifically, information on the name, address, and card for each virtual avatar mapped to a user are stored in the memory of the TV according to an embodiment of the present disclosure.

Therefore, when the virtual avatar (not shown) linked to the user exercising on the smart home mat enters the virtual store 2000 shown in FIG. 20(*a*), an entire TV screen 2001 changes to a virtual mall where the user is capable of selecting various products as shown in FIG. 20(*b*).

According to an embodiment of the present disclosure, after the virtual store 2000 is displayed on the TV screen, the intention of the user to enter the virtual store 2000 is automatically calculated based on the pressure exerted by the left and right feet of the user on the smart home mat. For example, if the virtual store 2000 is displayed on the TV screen and the user applies more pressure on the right foot on the smart home mat, it is determined that the user intends to enter the virtual store 2000 located on the right side of the virtual screen.

On the other hand, although not shown in FIG. 20, if the virtual store is displayed on the left side of the TV screen and the user applies more pressure on the left foot on the smart home mat, it is determined that the user intends to enter the virtual store located on the left side of the virtual screen.

When the user selects any item from items shown in FIG. 20(*b*) using a TV remote control, the purchase and order are processed immediately based on the information on the name, address, and card corresponding to the virtual avatar stored in the memory of the TV. To enhance authentication, the system is designed to additionally perform a facial recognition authentication process using a camera installed in the TV.

From the perspective of the service provider, by platformizing virtual space shopping, tenants may upload the advertisements and products thereof and monetize through rental fees or sales commissions.

In summary, the embodiments of the present disclosure provide virtual tracking services using the smart home mat within the home.

From the perspective of the smart home mat, the following services are possible.

First, changes in the foot pressure of the user may be checked using pressure sensors embedded in the smart home mat, thereby performing a body balance health check. In addition, the posture of the user may be checked using the camera installed in the TV, thereby predicting and screening for conditions such as senior Parkinson's disease in advance.

Second, the smart home mat is not limited to jogging. For example, the smart home mat according to an embodiment of the present disclosure may be placed in the living room, instead of the mat under the living room sofa. In this case, when the user sits on the sofa to watch the TV, the user feet may naturally rest on the smart home mat, thereby continuously sensing biometric signals. Thus, the smart home mat according to the embodiment of the present disclosure may also function as a wearable device.

Third, in the prior art, there is a problem of potential errors because the user is filmed by a TV camera while standing on the general floor. On the other hand, when the user stands on the smart home mat according to the embodiment of the present disclosure, the indoor position may be determined more accurately, thereby improving the accuracy of camera analysis.

Fourth, according to an embodiment of the present disclosure, comprehensive health management analysis services may be provided based on a combination of multiple sensors located within the home. For example, the body shape of the user may be analyzed through the TV camera, the body balance may be checked through the smart home mat (e.g., based on the pressure difference between the left and right feet), and biometric recognition may be enabled by a wearable device.

Fifth, remote medical consultation services may be provided at home by integrating the results from the fourth feature with hospital health check-up data.

From the perspective of the virtual tracking service, depending on the degree of on-the-spot walking or jogging movements of the user detected by the smart home mat, the movements displayed on the TV screen is synchronized, and the movements of the user detected by the smart home mat may also be synchronized with audio data played through TV speakers. For example, in the case of the virtual tracking service, if the TV screen includes an image of a snowy path, the sound of walking or running on snow (e.g., crunching sound) is played. Similarly, if the TV screen includes an image of rain, the sound of walking or running on water is played. Such a design also falls within the scope of the present disclosure.

Various embodiments may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal. The foregoing embodiments are merely exemplary and are not to be considered as limiting the present disclosure. The present teachings can be readily applied to other types of methods and apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

MODE

In the previous section titled "Best Mode," various embodiments of the present disclosure have been described, and it is understood that combining embodiments depicted in two or more drawings, as needed by those skilled in the art, also falls within the scope of the present disclosure.

INDUSTRIAL APPLICABILITY

As described above, since at least one of the embodiments of the present disclosure is applicable to a television (TV), wearable device, smart home mat, smart watch, and so on, the industrial applicability thereof is recognized.

The invention claimed is:

1. A method of controlling a system having a communicable smart home mat, the method comprising:

capturing an image of a user through a camera of a television (TV);

generating a virtual avatar based on the captured image;

outputting graphic images related to a virtual exercise environment to guide the user positioned on the smart home mat through a display of the TV; and controlling the graphic images related to the virtual exercise environment to be changed based on at least one of information on exercise amounts of the user or information on a health status of the user, wherein the method further comprises:

estimating an age group of the user positioned on the smart home mat through the camera of the TV; and based on that the age group of the user falls within a first range, change a body size of the virtual avatar, and wherein the body size of the virtual avatar is increased in response to the user having not exercised on the smart home mat for a specific period of time.

2. The method of claim 1, wherein the information on the exercise amounts of the user is determined based on at least one of a foot pressure or foot speed of the user recognized by the smart home mat.

3. The method of claim 2, wherein the smart home mat comprises at least one of a cover film, a ground electrode, foam, adhesive tape, or a sensor pattern.

4. The method of claim 1, wherein the information on the health status of the user is determined based on at least one of a heart rate, a blood pressure, or a blood sugar recognized by a wearable device worn by the user.

5. The method of claim 4, further comprising, based on the information on the health status of the user corresponds to a first level, displaying a graphic image guiding the user to change an exercise speed on the smart home mat.

6. The method of claim 5, further comprising, based on the information on the health status of the user corresponds to a second level:

displaying a graphic image guiding the user to stop exercise on the smart home mat; and sending an emergency call signal to a medical institution automatically.

7. The method of claim 1, further comprising:

storing the information on the exercise amounts of the user performed on the smart home mat in a memory; and displaying levels of physical changes of the user based on data stored in the memory.

8. The method of claim 1, further comprising:

based on that the age group of the user falls within a second range, change a color of a separate graphic image different from the virtual avatar.

9. The method of claim 1, further comprising:

in response to receiving a user command for editing a specific area of the virtual avatar, outputting exercise routines and amounts necessary to achieve a physique corresponding to the virtual avatar with the edited specific area.

10. A system comprising:

a smart home mat configured to obtain at least one of information on exercise amounts of a user or information on a health status of the user; and a television (TV) configured to:

capture an image of the user through a camera of the TV, generate a virtual avatar based on the captured image, output graphic images related to a virtual exercise environment to guide the user positioned on the smart home mat through a display of the TV, and control the graphic images related to the virtual exercise environment to be changed based on the at least one of information on exercise amounts of the user or information on the health status of the user, wherein the TV is further configured to:

estimate an age group of the user positioned on the smart home mat through the camera of the TV; and based on that the age group of the user falls within a first range, change a body size of the virtual avatar, and wherein the body size of the virtual avatar is increased in response to the user having not exercised on the smart home mat for a specific period of time.

* * * * *